(12) United States Patent
Mironov et al.

(10) Patent No.: US 12,708,726 B2
(45) Date of Patent: Aug. 18, 2026

(54) AEROSOL-GENERATING SYSTEM WITH LIQUID AEROSOL-FORMING SUBSTRATE IDENTIFICATION

(71) Applicant: Altria Client Services LLc, Richmond, VA (US)

(72) Inventors: Oleg Mironov, Cudrefin (CH); Ihar Nikolaevich Zinovik, Peseux (CH); Jerome Christian Courbat, Neuchatel (CH); Tony Reevell, London (GB)

(73) Assignee: Altria Client Services LLC, Richmond, VA (US)

( * ) Notice: Subject to any disclaimer, the term of this patent is extended or adjusted under 35 U.S.C. 154(b) by 905 days.

(21) Appl. No.: 17/537,272

(22) Filed: Nov. 29, 2021

(65) Prior Publication Data

US 2022/0086959 A1 Mar. 17, 2022

Related U.S. Application Data

(63) Continuation of application No. 15/429,659, filed on Feb. 10, 2017, now abandoned, which is a (Continued)

(30) Foreign Application Priority Data

Feb. 12, 2016 (EP) .................................... 16155571

(51) Int. Cl.
*A61M 15/06* (2006.01)
*A24F 40/10* (2020.01)
(Continued)

(52) U.S. Cl.
CPC ............ *A61M 15/06* (2013.01); *A24F 40/40* (2020.01); *A24F 40/50* (2020.01); *A24F 40/53* (2020.01);
(Continued)

(58) Field of Classification Search
CPC .......... A24F 40/10; A24F 40/40; A24F 40/50; A24F 40/53; A61M 11/042; A61M 15/06;
(Continued)

(56) References Cited

U.S. PATENT DOCUMENTS 1,555,803 A * 9/1925 Huber ...................... G01V 3/24 324/324
4,646,569 A * 3/1987 Cosser .................... G01F 23/24 307/118

(Continued)

FOREIGN PATENT DOCUMENTS

CN 103338664 A 10/2013
CN 104364621 A 2/2015

(Continued)

OTHER PUBLICATIONS

Office Action dated May 6, 2024 issued in Korean patent application No. 2018-7023140.

(Continued)

*Primary Examiner* — Edward F Landrum
*Assistant Examiner* — Adam M Eckardt
(74) *Attorney, Agent, or Firm* — Harness, Dickey & Pierce, P.L.C.

(57) ABSTRACT

An aerosol-generating system includes a storage portion configured to hold an aerosol-forming substrate, a first electrode, a second electrode spaced from the first electrode, and a control system. At least a portion of the storage portion is between the first electrode and the second electrode. The portion of the storage portion between the first electrode and the second electrode holds the aerosol-forming substrate when the aerosol-forming substrate is held in the storage portion. The control system is configured to measure an electrical quantity between the first electrode and the second electrode, and identify the liquid aerosol-forming substrate
(Continued)

held in the storage portion based on the measured electrical quantity information.

16 Claims, 5 Drawing Sheets

Related U.S. Application Data continuation of application No. PCT/EP2017/052916, filed on Feb. 9, 2017.

(51) Int. Cl.

| | |
|---|---|
| ***A24F 40/40*** | (2020.01) |
| ***A24F 40/50*** | (2020.01) |
| ***A24F 40/53*** | (2020.01) |
| ***G01N 27/06*** | (2006.01) |
| ***G01N 27/22*** | (2006.01) |
| ***H05B 1/02*** | (2006.01) |
| ***H05B 3/16*** | (2006.01) |

(52) U.S. Cl.

CPC ............ *G01N 27/06* (2013.01); *G01N 27/22* (2013.01); *H05B 1/0244* (2013.01); *H05B 3/16* (2013.01); *A24F 40/10* (2020.01)

(58) Field of Classification Search

CPC .... A61M 2205/3317; A61M 2205/502; A61M 2205/581; A61M 2205/587; A61M 2205/6018; B29C 45/02; B29C 45/586; G01N 27/06; G01N 27/07; G01N 27/22; G01N 27/226; H05B 1/0244; H05B 1/02; H05B 3/16

See application file for complete search history.

(56) References Cited

U.S. PATENT DOCUMENTS

| | | | | |
|---|---|---|---|---|
| 10,881,144 | B2 * | 1/2021 | Batista | A24F 40/42 |
| 2003/0000303 | A1 | 1/2003 | Livingston et al. | |
| 2013/0192615 | A1 | 8/2013 | Tucker et al. | |
| 2014/0182611 | A1 | 7/2014 | Liu | |
| 2014/0191054 | A1 * | 7/2014 | Hingley | G01F 23/241 239/74 |
| 2015/0122015 | A1 | 5/2015 | Leppard | |
| 2015/0235546 | A1 | 8/2015 | Stapleford | |
| 2016/0345628 | A1 * | 12/2016 | Sabet | H04M 1/21 |
| 2016/0354561 | A1 * | 12/2016 | McCullough | A24C 5/01 |

FOREIGN PATENT DOCUMENTS

| | | | | |
|---|---|---|---|---|
| EP | 2399636 | A1 * | 12/2011 | |
| EP | 2468116 | A1 | 6/2012 | |
| EP | 2493342 | A1 | 9/2012 | |
| JP | S55-147342 | A | 11/1980 | |
| JP | H04-350550 | A | 12/1992 | |
| JP | 2014-527614 | A | 10/2014 | |
| JP | 2015-524257 | A | 8/2015 | |
| TW | 201206357 | A | 2/2012 | |
| WO | WO-2012/174612 | A1 | 12/2012 | |
| WO | WO-2015/127429 | A1 | 8/2015 | |
| WO | WO-2015140312 | A1 * | 9/2015 | A24B 15/16 |
| WO | WO-2015177046 | A1 | 11/2015 | |
| WO | WO-2016/150922 | A2 | 9/2016 | |
| WO | WO-2017/045897 | A1 | 3/2017 | |

OTHER PUBLICATIONS

European Search Report for Application No. EP 16155571 dated Jul. 26, 2016.

International Search Report and Written Opinion for corresponding International Application No. PCT/EP2017/052916 dated Apr. 21, 2017.

International Preliminary Report on Patentability issued May 4, 2018 in International Application No. PCT/EP2017/052916.

Russian Notice of Allowance for corresponding Application No. 2018132351, dated Mar. 11, 2020, English translation thereof.

First Office Action and Search Report issued Sep. 18, 2020 in Chinese Application No. 201780007239.3.

Office Action dated Feb. 8, 2021 issued in corresponding Japanese Patent Application No. 2018-540716.

Japanese Office Action dated Jun. 17, 2021 for corresponding Japanese Application No. 2018-540716, and English-language translation thereof.

Notice of Allowance dated Aug. 12, 2024 issued in Korean Patent Application No. 10-2018-7023140.

* cited by examiner 320
322
323
324
321

330
332
334
333
335
331

342
340
343
341

W
P
W
I
344'
343'
Z
L
P
345'
346'
347'

343"
344"
345"
346"
347"

AEROSOL-GENERATING SYSTEM WITH LIQUID AEROSOL-FORMING SUBSTRATE IDENTIFICATION

This application is a continuation of U.S. application Ser. No. 15/429,659, filed on Feb. 10, 2017, which is a continuation of and claims priority to PCT/EP2017/052916 filed on Feb. 9, 2017, and further claims priority to EP 16155571.9 filed on Feb. 12, 2016 the contents of each of which are hereby incorporated by reference in their entirety.

BACKGROUND

At least one example embodiment relates to aerosol-generating systems and cartridges for aerosol-generating systems. The aerosol-generating systems may be electrically operated vaping systems.

One type of aerosol-generating system is an electrically operated vaping system. Electrically operated vaping systems typically comprise a liquid aerosol-forming substrate, which is atomized to form an aerosol. Electrically operated vaping systems often comprise a power supply, a liquid-storage portion for holding a supply of liquid aerosol-forming substrate and an atomizer or heater. A heater used in electronically operated vaping systems may comprise a coil of heater wire wound around an elongate wick soaked in liquid aerosol-forming substrate.

Liquid aerosol-forming substrates may have different compositions. Different compositions of liquid aerosol-forming substrates may have different properties. Some liquid aerosol-forming substrates may not be suitable for use with some aerosol-generating systems. Some liquid aerosol-forming substrates may be damaged or spoiled by high temperatures. Some liquid aerosol-forming substrates have relatively high viscosities and may not be effectively atomized by certain aerosol-generators.

A manufacturer of an aerosol-generating system may authorize certain liquid aerosol-forming substrates for use in their aerosol-generating systems. Authorized liquid aerosol-forming substrates may have suitable properties for use in the aerosol-generating system. However, an adult vaper may refill the liquid storage portion with an unauthorized and unsuitable liquid aerosol-forming substrate or may use an unauthorized cartridge holding an unauthorized and unsuitable liquid aerosol-forming substrate. Some unauthorized liquid aerosol-forming substrates may damage the aerosol-generating system. Some unauthorized liquid aerosol-forming substrates may be harmful to an adult vaper.

It would be desirable for an aerosol-generating system to be able to distinguish between liquid aerosol-forming substrates having different compositions. It would be desirable for an aerosol-generating system to be adjustable for use with different liquid aerosol-forming substrate compositions. It would be desirable for an aerosol-generating system to inform an adult vaper of authorized or unauthorized liquid aerosol-forming substrates held in the liquid storage portion.

SUMMARY

In at least one example embodiment, an aerosol-generating system comprises: a storage portion configured to hold an aerosol-forming substrate; a first electrode; a second electrode spaced from the first electrode; and a control system. The first electrode and the second electrode are arranged such that at least a portion of the storage portion is between the first electrode and the second electrode. The portion of the liquid storage portion between the first electrode and the second electrode stores the aerosol-forming substrate when aerosol-forming substrate is held in the storage portion. The control system is configured to: measure an electrical quantity between the first electrode and the second electrode, and identify the aerosol-forming substrate held in the storage portion based on the measured electrical quantity information.

Identifying the aerosol-forming substrate held in the storage portion may enable the aerosol-generating system or an adult vaper to identify an unsuitable, unauthorized, or unknown aerosol-forming substrate held in the storage portion. This may substantially prevent and/or reduce use of aerosol-forming substrates that may cause damage to the aerosol-generating system. This may substantially prevent and/or reduce use of liquid aerosol-forming substrates that are potentially harmful to the adult vaper. Identification of the liquid aerosol-forming substrate held in the liquid storage portion may also enable the aerosol-generating system to distinguish between suitable or authentic liquid aerosol-forming substrates. This may enable the aerosol-generating system to be operated in different modes depending on the identity of the liquid aerosol-forming substrate.

BRIEF DESCRIPTION OF THE DRAWINGS

Example embodiments will be further described, by way of example only, with reference to the accompanying drawings.

DETAILED DESCRIPTION

Figure 1:
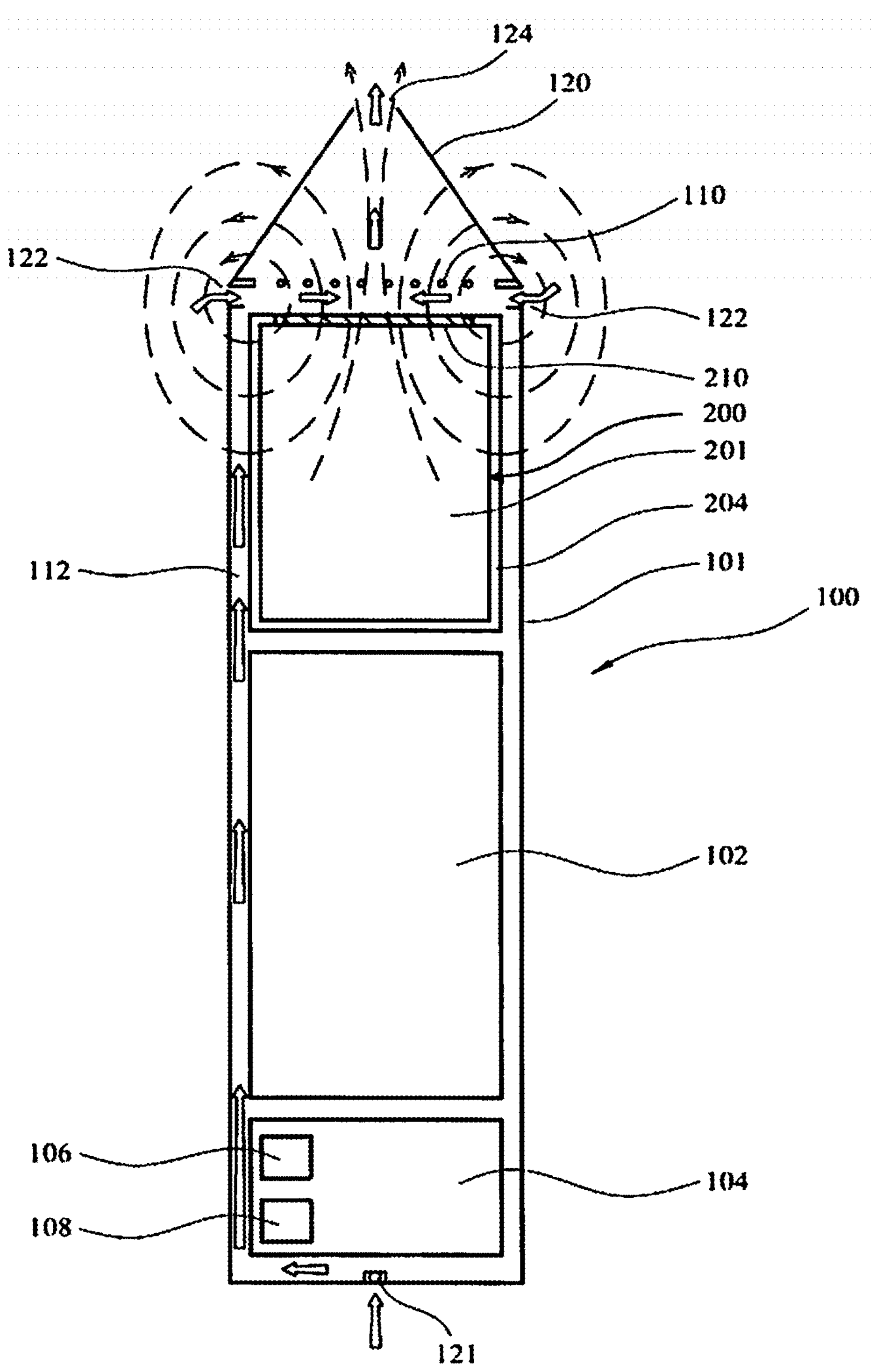
FIG. 1 is a schematic illustration of an aerosol-generating system according to at least one example embodiment.

Various example embodiments will now be described more fully with reference to the accompanying drawings in which some example embodiments are shown. However, specific structural and functional details disclosed herein are merely representative for purposes of describing example embodiments. Thus, the embodiments may be embodied in many alternate forms and should not be construed as limited to only example embodiments set forth herein. Therefore, it should be understood that there is no intent to limit example embodiments to the particular forms disclosed, but on the contrary, example embodiments are to cover all modifications, equivalents, and alternatives falling within the scope.

In the drawings, the thicknesses of layers and regions may be exaggerated for clarity, and like numbers refer to like elements throughout the description of the figures.

Although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that, if an element is referred to as being "connected" or "coupled" to another element, it can be directly connected, or coupled, to the other element or intervening elements may be present. In contrast, if an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," if used herein, specify the presence of stated features, integers, steps, operations, elements and/or components, but do not preclude the presence or addition of one or more other features, integers, steps, operations, elements, components and/or groups thereof.

Spatially relative terms (e.g., "beneath," "below," "lower," "above," "upper" and the like) may be used herein for ease of description to describe one element or a relationship between a feature and another element or feature as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, for example, the term "below" can encompass both an orientation that is above, as well as, below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

In order to more specifically describe example embodiments, various features will be described in detail with reference to the attached drawings. However, example embodiments described are not limited thereto.

As used herein with reference to example embodiments, the term ‘electrical quantity’ is used to describe any electrical property, parameter or attribute of a system that can be quantified by measurement. For example, suitable ‘electrical quantities’ include impedance, capacitance and resistance. The control system may be configured to measure at least one of impedance, capacitance and resistance.

As used herein with reference to the example embodiments, the term “identify” is used to describe verification, authentication or recognition of a liquid aerosol-forming substrate. For example, identifying a liquid aerosol-forming substrate may include determining at least one of the composition of the liquid aerosol-forming substrate, the suitability of the liquid aerosol-forming substrate for use in the aerosol-generating system and the origin or authenticity of the liquid aerosol-forming substrate. Similarly, as used herein, the term ‘identity’ is used to describe at least one of the composition, the suitability and the authenticity of the liquid aerosol-forming substrate.

Liquid aerosol-forming substrates may comprise one or more constituents. Liquid aerosol-forming substrates may comprise one or more main constituents, such as glycerine and propylene. Liquid aerosol-forming substrates may comprise substantially different proportions of the main constituents. Variations in the compositions and the proportions of the main constituents may substantially vary the electrical properties of liquid aerosol-forming substrates. The variation in the electrical properties of liquid aerosol-forming substrates may be such that a liquid aerosol-forming substrate may be identified by its electrical properties.

In at least one example embodiment, the aerosol-generating system comprises a liquid storage portion for holding a liquid aerosol-forming substrate. The electrical properties of the liquid storage portion may depend on the electrical properties of the liquid aerosol-forming substrate held in the liquid storage portion. The aerosol-generating system is configured to monitor an electrical property of the liquid storage portion. This is achieved by arranging at least a portion of the liquid storage portion holding liquid aerosol-forming substrate between a first electrode and a second electrode and configuring the control system to measure an electrical quantity between the first electrode and the second electrode. As such, the control system is configured to measure an electrical quantity across at least a portion of the liquid storage portion holding liquid aerosol-forming substrate (unless the liquid aerosol-forming substrate has been exhausted or depleted from the liquid storage portion). The control system is further configured to use the measurements of the electrical quantity to identify the liquid aerosol-forming substrate held in the liquid storage portion.

The liquid storage portion may hold liquid aerosol-forming substrate. The liquid storage portion may also comprise one or more of: air held in the liquid storage portion, a carrier material for holding the liquid aerosol-forming substrate, and a housing for holding the liquid aerosol-forming substrate. The liquid aerosol-forming substrate, air, carrier material and housing may have different electrical properties.

The liquid storage portion may comprise an electrical load. The liquid storage portion may comprise at least one of a resistive load and a capacitive load. Electrical quantities of resistive and capacitive loads may be measured without requiring complex electronics.

The first and second electrodes may be arranged such that liquid aerosol-forming substrate held in the liquid storage portion is between the first and second electrodes. The first and second electrodes may also be arranged such that one or more of the air held in the liquid storage portion, the carrier material, and the housing are arranged between the second electrodes. The first and second electrodes may be arranged in contact with liquid aerosol-forming substrate held in the liquid storage portion. The first and second electrodes may be arranged in contact with the carrier material. The first and second electrodes may be arranged in contact with the housing.

Liquid aerosol-forming substrates produced or approved by a manufacturer of an aerosol-generating system may comprise constituents that produce specific, recognizable electrical quantity information when measured by the control system. The control system may be configured to identify whether the liquid aerosol-forming substrate held in the liquid storage portion is a liquid aerosol-forming substrate produced or approved by the manufacturer. In other words, the control system may be configured to determine whether the liquid aerosol-forming substrate is authentic.

More than one liquid aerosol-forming substrate may be suitable for use in the aerosol-generating system. Liquid aerosol-forming substrates having compositions that are suitable for use in an aerosol-generating system may produce one or more ranges of specific, recognizable electrical quantity information when measured by the control system. The control system may be configured to differentiate between liquid aerosol-forming substrates that are suitable for use in the aerosol-generating system and liquid aerosol-forming substrates that are unsuitable for use in the aerosol-generating system based on the measured electrical quantity information. In other words, the control system may be configured to identify whether the measured electrical quantity information matches an expected value or range of values for a liquid aerosol-forming substrate that is suitable for use in the aerosol-generating system.

The control system may be configured to determine the composition of the liquid aerosol-forming substrate based on the measured electrical quantity information. Certain constituents of a liquid aerosol-forming substrate may substantially affect the electrical properties of a liquid aerosol-forming substrate. A manufacturer may produce two or more liquid aerosol-forming substrates comprising different proportions of a constituent that substantially affects the electrical properties of a liquid aerosol-forming substrate. The control system may be configured to distinguish between the two or more liquid aerosol-forming substrates produced or authorized by the manufacturer based on the measured electrical quantity information.

The control system may be configured to identify the liquid aerosol-forming substrate held in the liquid storage portion by comparison. The control system may be configured to compare the measured electrical quantity information to reference electrical quantity information stored in the control system.

Reference electrical quantity information may be stored in a memory of the control system. The reference electrical quantity information may be electrical quantity information measured by the control system and stored in a memory of the control system. The reference electrical quantity information may be associated with liquid aerosol-forming substrate identity information. This may enable the identification of the liquid aerosol-forming substrate held in the liquid storage portion to be reliable.

The reference electrical quantity information may comprise a plurality of ranges of reference electrical quantity information. Each range of the reference electrical quantity information may be associated with a liquid aerosol-forming substrate. The control system may be configured to compare and match measured electrical quantity information to a stored range of reference electrical quantity information.

The reference electrical quantity information may comprise one or more desired (or, alternatively a predetermined) thresholds. The control system may be configured to compare the measured electrical quantity information to the one or more desired (or, alternatively a predetermined) thresholds. The control system may be configured to identify the liquid aerosol-forming substrate if the measured electrical quantity information does not exceed the one or more thresholds. The control system may be configured to identify the liquid aerosol-forming substrate held in the liquid storage portion as a suitable, authorized or authentic liquid aerosol-forming substrate when the measured electrical quantity information does not exceed a desired (or, alternatively a predetermined) threshold. The control system may be configured to identify the liquid aerosol-forming substrate held in the liquid storage portion as an unsuitable, unauthorized or an unknown liquid aerosol-forming substrate when the measured electrical quantity information exceeds a desired (or, alternatively a predetermined) threshold.

As used herein, a measurement that exceeds a desired (or, alternatively a predetermined) threshold may be one of a value that is above the desired (or, alternatively a predetermined) threshold or a value that is below the desired (or, alternatively a predetermined) threshold. In other words, a value that does not exceed the desired (or, alternatively a predetermined) threshold is a value that is within a desired (or, alternatively a predetermined) range.

The reference electrical quantity information may be stored in a lookup table. The lookup table may comprise stored reference electrical quantity information and stored liquid aerosol-forming substrate identity information. The stored reference electrical quantity information may be associated with the stored liquid aerosol-forming substrate identity information. The stored liquid aerosol-forming substrate identity information may comprise one or more of composition information, authenticity information and suitability information.

The control system may be configured to indicate to an adult vaper the determined identity of liquid aerosol-forming substrate held in the liquid storage portion.

The aerosol-generating system may further comprise an aerosol-generator configured to receive liquid aerosol-forming substrate from the liquid storage portion. The control system may be further configured to control operation of the aerosol-generator based on the determined identity of the liquid aerosol-forming substrate held in the liquid storage portion. This may enable the aerosol-generating system to operate the aerosol-generator in different modes, such as at different temperatures that are most appropriate for different compositions of liquid aerosol-forming substrates. This may enable the aerosol-generating system to disable and/or substantially prevent operation of the aerosol-generator if an unsuitable, unauthorized or unknown liquid aerosol-generating substrate is identified.

As used herein with reference to the example embodiments, controlling operation of the aerosol-generator includes, amongst other things: controlling the power supplied to the aerosol-generator, controlling the temperature of the aerosol-generator, controlling the duration of operation of the aerosol-generator, and disabling and/or substantially preventing operation of the aerosol-generator.

The control system may be configured to measure the electrical quantity between the first electrode and the second electrode and identify the liquid aerosol-forming substrate held in the liquid storage portion independently of operation the aerosol-generator. This may enable the control system to control operation of the aerosol-generator before the aerosol-generator is operated. This may substantially prevent and/or reduce damage to the aerosol-generator from atomization of an unsuitable liquid aerosol-forming substrate.

The first electrode and the second electrode may be arranged at any suitable location relative to the liquid storage portion. The first electrode and the second electrode may be arranged at or in the liquid storage portion. The first electrode and the second electrode may be arranged at or on the housing. Where the housing of the liquid storage portion forms a cavity for holding the liquid aerosol-forming substrate, the first electrode and the second electrode may be arranged at or in the cavity.

The aerosol-generating system may comprise one or more pairs of first and second electrodes. The aerosol-generating system may comprise two or more pairs of electrodes arranged such that different portions of the liquid storage portion are arranged between the first and second electrodes. Providing multiple pairs of electrodes may improve the reliability of the measurements. The one or more pairs of first and second electrodes may comprise part of a sensor.

The electrodes may be any suitable type of electrode. For example, suitable types of electrodes include point electrodes, ring electrodes, plate electrodes or track electrodes. The first electrode and the second electrode may be the same type of electrode. The first electrode and the second electrode may be different types of electrode.

The electrodes may by any suitable shape. For example, the electrodes may be: square, rectangular, curved, arcuate, annular, spiral or helical. The electrodes may be substantially cylindrical. The electrodes may comprise one or more sections that are substantially linear, non-linear, planar or non-planar. The electrodes may be rigid. This may enable the electrodes to maintain their shape. The electrodes may be flexible. This may enable the electrodes to conform to the shape of the liquid storage portion. The electrodes may be configured to conform to the shape of a housing of the liquid storage portion.

The electrodes may have a length, a width, and a thickness. The length of the electrodes may be substantially greater than the width of the electrodes. In other words, the electrodes may be elongate. The thickness of the electrodes may be substantially less than the length and the width of the electrodes. In other words, the electrodes may be thin. Thin electrodes and elongate electrodes may have a larger surface area to volume ratio. This may improve the sensitivity of measurements.

The electrodes may comprise any suitable material. The electrodes may comprise any suitable electrically conductive material. Suitable electrically conductive materials include metals, alloys, electrically conductive ceramics and electrically conductive polymers. As used herein with respect to example embodiments, an electrically conductive material refers to a material having a volume resistivity at 20° C. of less than about $1\times10^{-5}$ Ωm, or ranging from about $1\times10^{-5}$ Ωm to about $1\times10^{-9}$ Ωm. The materials may include gold and platinum. The electrodes may be coated with a passivation layer. The electrodes may comprise or be coated in material that is sufficiently non-reactive so as not to react with or contaminate the liquid aerosol-forming substrate. The electrodes may comprise transparent or translucent material. For example, a suitable transparent material may be Indium Tin Oxide (ITO).

The electrodes may be arranged in any suitable arrangement relative to the liquid storage portion. The electrodes may be arranged in the liquid storage portion. The first electrode and the second electrode may be arranged at opposite sides of the liquid storage portion. The first electrode and the second electrode may be arranged at opposite ends of the liquid storage portion. Where the liquid-storage portion comprises a carrier material, the electrodes may be arranged in contact with the carrier material. Where the liquid storage portion comprises a housing, at least one of the first and second electrodes may be arranged at or in contact with the housing. The first and second electrodes may be substantially cylindrical. The first electrode may be arranged to substantially surround the second electrode. The first and second electrodes may be arranged concentrically about a common axis.

At least one of the first electrode and the second electrode may be arranged on a platform. The platform may comprise electrically insulating material. Where the liquid storage portion comprises a housing, the platform may be separate from the housing. The platform may be arranged on the housing. The platform may form a portion of the housing. The platform may comprise the same material as the housing. The platform may comprise a different material to the housing.

The platform may comprise any suitable electrically insulating material. For example, suitable electrically insulating materials include glasses, plastics and ceramic materials. As used herein with respect to example embodiments, an electrically insulating material refers to a material having a volume resistivity at 20° C. of greater than about $1\times10^{6}$ Ωm, or ranging from about $1\times10^{9}$ Ωm to about $1\times10^{21}$ Ωm.

The electrodes may be secured on the platform. The electrodes may be secured on the platform by any suitable means. In at least one example embodiment, the electrodes may be secured on the platform by a bonding material, such as an adhesive. The electrodes may be deposited on the platform by any suitable method of deposition. The electrodes may be etched in the platform.

The second electrode may be spaced apart from the first electrode. This may substantially prevent and/or reduce direct contact between the first electrode and the second electrode. The spacing between the first electrode and the second electrode may be consistent along the length of the first electrode and the second electrode. Where the first electrode and the second electrode are arranged at opposite sides of the liquid storage portion, the spacing may be about the width of the liquid storage portion. The spacing between the first electrode and the second electrode may range from about 1 μm to about 1 mm, range from about 1 μm to about 500 μm, or range from about 10 μm to about 100 μm.

The second electrode may substantially follow the path of the first electrode. This may enable the spacing between the first and second electrodes to remain substantially consistent along the length of the first and second electrodes. The second electrode may be arranged substantially parallel to the first electrode.

The first electrode and the second electrode may be interdigitated. The first electrode may comprise a plurality of protrusions and interspaces and the second electrode may comprise a plurality of protrusions and interspaces. The protrusions of the first electrode may extend into the interspaces of the second electrode and the protrusions of the second electrode may extend into the interspaces of the first electrode. Interdigitating the electrodes may minimise the spacing between the electrodes. This may improve the sensitivity of the measurements.

The protrusions of the first and second electrodes may be substantially linear. The protrusions of the first electrode may extend substantially in a first direction and the protrusions of the second electrode may extend substantially in a second direction. The first and second electrodes may be arranged with the first direction substantially parallel to the second direction. The protrusions may be substantially non-linear. The protrusions may be curved or arcuate. For example, a suitable sensor comprising interdigitated electrodes may be of the type DRP-G-IDEPT10 from DropSens™.

The aerosol-generating system may comprise an aerosol-generator including one or more aerosol-generating elements. The one or more aerosol-generating elements may comprise one or more heating elements. The one or more aerosol-generating elements may comprise one or more vibratable elements. Where the aerosol-generator comprises one or more aerosol-generating elements, at least one of the aerosol-generating elements may comprise one of the electrodes. Forming one of the electrodes as part of the aerosol-generator may reduce the number of components required to manufacture the aerosol-generating system.

The control system may comprise electric circuitry. The electric circuitry may comprise a microprocessor, which may be a programmable microprocessor. The electric circuitry may comprise further electronic components. The electric circuitry may be configured to regulate a supply of power to the first electrode and the second electrode.

The control system may be configured to control or regulate a supply of power to the first electrode and the second electrode. The control system may be configured to control or regulate a supply of power to the aerosol-generator. A first control system may be configured to control or regulate the supply of power to the first electrode and the second electrode and a second control system may be configured to control or regulate the supply of power to the aerosol-generator.

Power may be supplied substantially continuously to the first electrode and the second electrode. Power may be supplied to the first electrode and the second electrode following activation of the system. Power may be supplied to the first electrode and the second electrode in the form of pulses of electrical current. Power may be supplied to the first electrode and the second electrode intermittently, such as on a puff-by-puff basis.

The control system may be configured to supply a measurement signal to the first electrode and the second electrode. The control system may be configured to supply a continuous measurement signal to the first electrode and the second electrode. In other words, the control system may be configured to supply a direct voltage to the first electrode and the second electrode. This may require less complex circuitry than supplying an oscillating measurement signal, such as an alternating voltage. Where the control system is configured to supply a substantially continuous measurement signal, the control system may be further configured to measure electrical resistance between the first electrode and the second electrode.

The control system may be configured to supply an oscillating measurement signal to the first electrode and the second electrode. In other words, the control system may be configured to supply an alternating voltage to the first and second electrodes. The control system may be configured to supply an oscillating measurement signal to the first electrode and the second electrode at a desired (or, alternatively a predetermined) frequency. The desired (or, alternatively a predetermined) frequency may be any suitable frequency for the control system to measure the electrical quantity between the first electrode and the second electrode. The desired (or, alternatively a predetermined) frequency may be equal to or less than about 20 MHz, or equal to or less than about 10 MHz. The desired (or, alternatively a predetermined) frequency may range from about 10 kHz to about 10 MHz, range from about 10 kHz to about 1 MHz, or range from about 100 kHz to about 1 MHz.

Some liquid storage portions comprising different combinations of one or more carrier materials, liquid aerosol-forming substrates and air may react similarly in response to an oscillating measurement signals at a particular frequency. In at least one example embodiment, on application of an oscillating measurement signal at a particular frequency to the first electrode and the second electrode, the electrical quantity measured for a first liquid storage portion, comprising a first liquid aerosol-forming substrate, may be the same as the electrical quantity measured for a second liquid storage portion, comprising a second liquid aerosol-forming substrate, having a different composition to the first liquid aerosol-forming substrate. Such similar reactions may cause errors in the identification of the liquid aerosol-forming substrate held in a liquid storage portion.

Although the reaction of some different liquid storage portions may be the same in response to an oscillating measurement signal at a particular frequency, the reaction of these different liquid storage portions may vary in response to an oscillating measurement signal at a different frequency. In at least one example embodiment, on the application of an oscillating measurement signal at a first frequency, the electrical quantity measured for a first liquid storage portion and a second liquid storage portion may be the same, and on the application of an oscillating measurement signal at a second frequency, the electrical quantity measured for the first liquid storage portion may be different to the electrical signal measured for the second liquid storage portion.

Similarly, the reaction of different liquid storage portions to the application of a continuous measurement signal, such as a direct voltage, may also be the same for certain liquid storage portions and different for other liquid storage portions.

Therefore, in at least one example embodiment, the control system may be configured to apply more than one measurement signal to the first and second electrode and to identify the liquid aerosol-forming substrate based on measurements of the electrical quantity using different measurement signals. In at least one example embodiment, the control system may be configured to apply oscillating measurement signals to the first electrode and the second electrode at more than one frequency. The control system may be configured to apply a first oscillating measurement signal to the first and second electrodes at a first frequency and to apply a second oscillating measurement signal to the first and second electrodes at a second frequency. The control system may be configured to apply one or more oscillating measurements signals to the first and second electrodes and a continuous measurement signal to the first and second electrodes. This may improve the accuracy of the identification of the liquid aerosol-forming substrate held in the liquid storage portion. This may reduce the likelihood of determining the wrong identity of the liquid aerosol-forming substrate held in the liquid storage portion. The control system may be configured to identify the liquid aerosol-forming substrate held in the liquid storage portion when the aerosol-generating system is switched on. The control system may be configured to identify the liquid aerosol-forming substrate held in the liquid storage portion periodically at desired (or, alternatively a predetermined) intervals. The control system may be configured to identify the liquid aerosol-forming substrate held in the liquid storage portion when prompted by an adult vaper.

The aerosol-generating system may comprise a power supply. The aerosol-generating system may comprise a power supply arranged to supply power to the control system, the first electrode and the second electrode and the aerosol-generator. The aerosol-generator may comprise a single power supply. The aerosol-generator may comprise a first power supply arranged to supply power to the first electrode and the second electrode and a second power supply configured to supply power to the aerosol-generator.

During vaping, liquid aerosol-forming substrate held in the liquid storage portion is consumed and replaced with air. Liquid aerosol-forming substrates typically have substantially different electrical properties to air. Therefore, the amount of liquid aerosol-forming substrate held in the liquid storage portion may affect the electrical properties of the liquid storage portion. This may affect the measurement of the electrical quantity between the first electrode and the second electrode and the identification of the liquid aerosol-forming substrate. The control system may be configured to determine the amount of liquid aerosol-forming substrate held in the liquid storage portion. The control system may be configured to adjust the identification of the liquid aerosol-forming substrate based on the amount of liquid aerosol-forming substrate held in the liquid storage portion. In other words, the control system may be configured to compensate for the amount of liquid aerosol-forming substrate held in the liquid storage portion.

The control system may be configured to identify the liquid aerosol-forming substrate held in the liquid storage portion when prompted by an indication for the adult vaper that the liquid storage portion is full. The aerosol-generating system may comprise a switch that is pressable by an adult vaper to indicate to the control system that the aerosol-generating system is full.

The control system may comprise any suitable measuring device configured to measure the electrical quantity between the first electrode and the second electrode. In at least one example embodiment, the control system may comprise a bridge circuit configured to measure the electrical quantity between the first electrode and the second electrode. The bridge circuit may be any suitable bridge circuit known in the art, such as a Wheatstone bridge or a Wien bridge. The control system may comprise an LCR meter.

The electrical quantity to be measured by the control system may be impedance. The impedance between the first electrode and the second electrode may depend on the composition of the liquid aerosol-forming substrate held in the liquid storage portion.

The impedance may be measured directly by the control system. The impedance may be calculated. In at least one example embodiment, the impedance may be calculated from measurements of the magnitude of the voltage and the current between the electrodes, and measurements of the phase difference between the current and voltage. The identity of the liquid aerosol-forming substrate held in the liquid storage portion may be determined from the measured or calculated impedance.

The electrical quantity to be measured by the control system may be resistance. The resistance between the first electrode and the second electrode may depend on the composition of the liquid aerosol-forming substrate held in the liquid storage portion. The resistivity between the first electrode and the second electrode may depend on the liquid aerosol-forming substrate held in the liquid storage portion. The portion of the liquid storage portion arranged between the first electrode and the second electrodes may comprise a resistive load.

The resistance may be measured where the liquid aerosol-forming substrate comprises conductive materials.

The resistance may be calculated from measurements of the magnitude of the voltage and the current and the phase difference between the voltage and the current. The resistance may be determined from measurements of the impedance. The identity of the liquid aerosol-forming substrate held in the liquid storage portion may be calculated from the measured or calculated resistance.

The electrical quantity to be measured by the control system may be capacitance where the aerosol-forming substrate comprises dielectric materials.

The capacitance between the first electrode and the second electrode may depend on the composition of the liquid aerosol-forming substrate held in the liquid storage portion. The permittivity between the first electrode and the second electrode may depend on the composition of the liquid aerosol-forming substrate held in the liquid storage portion. The portion of the liquid storage portion arranged between the first electrode and the second electrode may comprise a capacitive load. The first electrode and the second electrode may form a capacitor. The first electrode may form a first capacitor plate and the second electrode may form a second capacitor plate. Liquid aerosol-forming substrate held in the liquid storage portion may form part of the dielectric of the capacitor. The capacitive load between the first electrode and the second electrode may have a capacitance in the picofarad (pF) range. This may enable fast charging and discharging times of the capacitor, and enable fast measurements of the capacitance.

The capacitance may be measured. In at least one example embodiment, the control system may comprise a capacitance measuring device configured to measure charge and discharge times of the capacitor comprising the first and second electrodes. The control system may comprise a timer circuit, such as a 555 timer circuit, and may be configured to determine capacitance based on the frequency of the timer circuit output.

The capacitance may be calculated. In at least one example embodiment, the capacitance may be calculated from measurements of the magnitude of the voltage and the current between the first and second capacitor plates. The capacitance may be calculated from measurements of the impedance. The identity of the liquid aerosol-forming substrate held in the liquid storage portion may be calculated from the measured or calculated capacitance.

The electrical quantity to be measured by the control system may depend on the size of the first and second electrodes and on the separation between the first and second electrodes. In at least one example embodiment, capacitance is a function of the separation between the first and second capacitor plates and the shape and size of the first and second capacitor plates. To ensure that a change in the electrical quantity being measured is not the result of a change in the shape or separation of the first and second electrodes, the first and second electrodes may be rigid and secured to a rigid platform or housing. The capacitor plates may comprise solid metal plates or thin walled metal sheets attached to a supporting substrate. The supporting substrate may be arranged between the capacitor plates to form part of the dielectric between the capacitor plates. The substrate may be arranged on the outside of the capacitor plates.

The liquid storage portion may be any suitable shape and size. In at least one example embodiment, the liquid storage portion may be substantially cylindrical. The cross-section of the liquid storage portion may, for example, be substantially circular, elliptical, square or rectangular.

The liquid storage portion may comprise a housing. The housing may comprise a base and one or more sidewalls extending from the base. The base and the one or more sidewalls may be integrally formed. The base and one or more sidewalls may be distinct elements that are attached or secured to each other. The housing may be a rigid housing. As used herein, the term 'rigid housing' is used to mean a housing that is self-supporting. The rigid housing of the liquid storage portion may provide mechanical support to the aerosol-generator. The liquid storage portion may comprise one or more flexible walls. The flexible walls may be configured to adapt to the volume of the liquid aerosol-forming substrate held in the liquid storage portion. The housing of the liquid storage portion may comprise any suitable material. The liquid storage portion may comprise substantially fluid impermeable material. The housing of the liquid storage portion may comprise a transparent or a translucent portion, such that liquid aerosol-forming substrate held in the liquid storage portion may be visible to an adult vaper through the housing.

The liquid storage portion may be configured such that aerosol-forming substrate held in the liquid storage portion is protected from ambient air. The liquid storage portion may be configured such that aerosol-forming substrate stored in the liquid storage portion is protected from light. This may substantially reduce the risk of degradation of the substrate and may maintain a high level of hygiene.

The liquid storage portion may be substantially sealed. The liquid storage portion may comprise one or more outlets for liquid aerosol-forming substrate held in the liquid storage portion to flow from the liquid storage portion to the aerosol-generator. The liquid storage portion may comprise one or more semi-open inlets. This may enable ambient air to enter the liquid storage portion. The one or more semi-open inlets may be semi-permeable membranes or one way valves, permeable to allow ambient air into the liquid storage portion and impermeable to substantially prevent air and liquid inside the liquid storage portion from leaving the liquid storage portion. The one or more semi-open inlets may enable air to pass into the liquid storage portion under specific conditions.

The liquid storage portion may comprise at least one channel configured to hold the liquid aerosol-forming substrate. The at least one channel may be configured such that capillary forces act on the liquid aerosol-forming substrate. The capillary force acting on the liquid aerosol-forming substrate may hold the level of the liquid aerosol-forming substrate substantially perpendicular to at least one of the sidewalls of the liquid storage portion and the first and second electrodes. One dimension of the channel may be less than a desired (or, alternatively a predetermined) value, such that capillary forces act on liquid aerosol-forming substrate held in the channel. The dimension of the one or more channels may be the width of the one or more channel. The desired (or, alternatively a predetermined) value may be below about 3 mm, below about 2 mm, below about 0.5 mm, or below about 0.25 mm.

The liquid storage portion may comprise aerosol-forming substrate held in the liquid storage portion. As used herein with reference to the example embodiments, an aerosol-forming substrate is a substrate capable of releasing volatile compounds that can form an aerosol. Volatile compounds may be released by heating the aerosol-forming substrate. Volatile compounds may be released by moving the aerosol-forming substrate through passages of a vibratable element.

The aerosol-forming substrate may be liquid. The aerosol-forming substrate may be liquid at room temperature. The liquid aerosol-forming substrate may comprise both liquid and solid components. The aerosol-forming substrate may comprise nicotine. The nicotine containing liquid aerosol-forming substrate may be a nicotine salt matrix. The aerosol-forming substrate may comprise plant-based material. The aerosol-forming substrate may comprise tobacco. The aerosol-forming substrate may comprise a tobacco-containing material containing volatile tobacco flavor compounds, which are released from the aerosol-forming substrate upon heating. The aerosol-forming substrate may comprise homogenized tobacco material. The aerosol-forming substrate may comprise a non-tobacco-containing material. The aerosol-forming substrate may comprise homogenized plant-based material.

The liquid aerosol-forming substrate may comprise at least one aerosol-former. An aerosol-former is any suitable known compound or mixture of compounds that, during vaping, facilitates formation of a dense and stable aerosol and that is substantially resistant to thermal degradation at the temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Aerosol formers may be polyhydric alcohols or mixtures thereof, such as triethylene glycol, 1,3-butanediol and glycerine. The liquid aerosol-forming substrate may comprise other additives and ingredients, such as flavorants.

The liquid aerosol-forming substrate may comprise water, solvents, ethanol, plant extracts and natural or artificial flavors. The liquid aerosol-forming substrate may comprise one or more aerosol formers. Examples of suitable aerosol formers include glycerine and propylene glycol.

The liquid aerosol-forming substrate may comprise nicotine and at least one aerosol former. The aerosol former may be glycerine. The aerosol-former may be propylene glycol. The aerosol former may comprise both glycerine and propylene glycol. The liquid aerosol-forming substrate may have a nicotine concentration ranging from about 0.5% to about 10%. In at least one example embodiment, the nicotine concentration is about 2%.

The liquid aerosol-forming substrate may contain a mixture of dielectric materials, each with a separate dielectric constant (k). The main constituents of a liquid aerosol-forming substrate at room temperature, about 20° C., may include: glycerine (k~42), propylene glycol (k~32), water (k~80), air (k~1), nicotine and flavorants. Where the liquid aerosol-forming substrate forms a dielectric material, the electrical quantity to be measured by the control system may be capacitance.

The liquid aerosol-forming substrate may comprise a mixture of electrically conductive materials. Where the liquid aerosol-forming substrate forms an electrically conductive material, the electrical quantity to be measured by the control system may be resistance.

The liquid storage portion may comprise a carrier material within the housing. The carrier material is configured to hold the liquid aerosol-forming substrate. The liquid aerosol-forming substrate may be adsorbed or otherwise loaded onto the carrier material. Liquid aerosol-forming substrate absorbed in the material may spread or permeate through the carrier material, and changes in the saturation of the carrier material affect the entire body of carrier material. This may enable first and second electrodes arranged in contact with a portion of the carrier material to sense changes in the electrical quantity of the entire body of carrier material. This may enable the control system to measure the electrical quantity of the entire liquid storage portion.

The carrier material may be made from any suitable absorbent body of material, for example, a foamed metal or plastics material, polypropylene, terylene, nylon fibres or ceramic. The aerosol-forming substrate may be retained in the carrier material prior to vaping of the aerosol-generating system. The aerosol-forming substrate may be released into the carrier material during vaping. The aerosol-forming substrate may be released into the carrier material immediately prior to vaping. In at least one example embodiment, the liquid aerosol-forming substrate may be provided in a capsule. The shell of the capsule may melt upon heating by the heating element and releases the liquid aerosol-forming substrate into the carrier material. The capsule may contain a solid in combination with the liquid.

The liquid aerosol-forming substrate may be held in a capillary material. A capillary material is a material that actively conveys liquid from one end of the material to another. The capillary material may draw liquid aerosol-forming substrate to a specific location in the liquid storage portion, regardless of the orientation of the liquid storage portion. This may facilitate arrangement of the first and second electrodes for accurate and reliable determination of the identity of the liquid aerosol-forming substrate held in the liquid storage portion.

The capillary material may be configured to convey the aerosol-forming substrate to the aerosol-generator. The capillary material may be configured to convey the aerosol-forming substrate to the first and second electrodes. The capillary material may have a fibrous structure. The capillary material may have a spongy structure. The capillary material may comprise a bundle of capillaries. The capillary material may comprise a plurality of fibers. The capillary material may comprise a plurality of threads. The capillary material may comprise fine bore tubes. The fibers, threads or fine-bore tubes may be generally aligned to convey liquid to an atomizer. The capillary material may comprise a combination of fibers, threads and fine-bore tubes. The capillary material may comprise sponge-like material. The capillary material may comprise foam-like material. The structure of the capillary material may form a plurality of small bores or tubes, through which the liquid can be transported by capillary action.

The capillary material may comprise any suitable material or combination of materials. Examples of suitable materials are a sponge or foam material, ceramic- or graphite-based materials in the form of fibers or sintered powders, foamed metal or plastics materials, a fibrous material, for example made of spun or extruded fibres, such as cellulose acetate, polyester, or bonded polyolefin, polyethylene, terylene or polypropylene fibers, nylon fibers or ceramic. The capillary material may have any suitable capillarity and porosity so as to be used with different liquid physical properties. The liquid aerosol-forming substrate has physical properties, including but not limited to viscosity, surface tension, density, thermal conductivity, boiling point and vapour pressure, which allow the liquid to be transported through the capillary material by capillary action.

The aerosol-generator may be configured to receive aerosol-forming substrate from the liquid storage portion. The aerosol-generator may be an atomizer and/or a vaporizer. The aerosol-generator may comprise one or more aerosol-generating elements. The aerosol-generator may be configured to vaporize received aerosol-forming substrate using heat. The aerosol-generator may comprise a heating element configured to vaporize received liquid aerosol-forming substrate. The aerosol-generator may be configured to atomize received aerosol-forming substrate using ultrasonic vibrations. The aerosol-generator may comprise an ultrasonic transducer. The one or more aerosol-generating elements may comprise one or more vibratable elements.

The aerosol-generator may comprise a heating element configured to heat the aerosol-forming substrate. The heating element may comprise one or more heating elements. The one or more heating elements may be arranged appropriately so as to most effectively heat received aerosol-forming substrate. The one or more heating elements may be configured to heat the aerosol-forming substrate primarily by conduction. The one or more heating elements may be substantially in direct contact with the aerosol-forming substrate. The one or more heating elements may be arranged to transfer heat to the aerosol-forming substrate via one or more heat conductive elements. The one or more heating elements may be arranged to transfer heat to ambient air drawn through the aerosol-generating system during vaping, which may heat the aerosol-forming substrate by convection. The one or more heating elements may be arranged to heat the ambient air before it is drawn through the aerosol-forming substrate. The one or more heating elements may be arranged to heat the ambient air after it is drawn through the aerosol-forming substrate.

The heating elements may be an electric heater. The electric heater may comprise one or more electric heating elements. The one or more electric heating elements may comprise an electrically resistive material. Suitable electrically resistive materials may include: semiconductors such as doped ceramics, electrically "conductive" ceramics (such as, for example, molybdenum disilicide), carbon, graphite, metals, metal alloys and composite materials made of a ceramic material and a metallic material.

The one or more electric heating elements may take any suitable form. In at least one example embodiment, the one or more electric heating elements may take the form of one or more heating blades. The one or more electric heating elements may take the form of a casing or substrate having different electro-conductive portions, or one or more electrically resistive metallic tube.

The liquid storage portion may incorporate one or more disposable heating elements. The one or more electric heating elements may comprise one or more heating needles or rods that run through the aerosol-forming substrate. The one or more electric heating elements may comprise one or more flexible sheets of material. The electric heating element may comprise one or more heating wires or filaments, for example nickel-chromium (Ni—Cr), platinum, tungsten or alloy wires, or heating plates. The one or more heating elements may be deposited in or on a rigid carrier material.

The one or more heating elements may comprise one or more heat sinks or heat reservoirs. The one or more heat sinks or heat reservoirs may comprise a material capable of absorbing and storing heat and subsequently releasing the heat over time to heat the aerosol-forming substrate.

The heating elements may be substantially flat to allow for straightforward manufacture. As used herein, the term 'substantially flat' means formed in a single plane and not wrapped around or otherwise confirmed to fit a curved or other non-planar shape. A flat heating elements may be easily handled during manufacture and provide for a robust construction.

The heating elements may be of the type described in EP-B1-2493342, the entire content of which is incorporated herein by reference thereto. In at least one example embodiment, the heating elements may comprise one or more electrically conductive tracks on an electrically insulating substrate. The electrically insulating substrate may comprise any suitable material, and may be a material that is able to tolerate high temperatures (in excess of 300° C.) and rapid temperature changes. An example of a suitable material is a polyimide film, such as Kapton®.

The heating elements may be configured to heat a small amount of liquid aerosol-forming substrate at a time. The heating elements configured to heat a small amount of liquid aerosol-forming substrate at a time may include, for example, a liquid passageway in communication with the liquid aerosol-forming substrate. The liquid aerosol-forming substrate may be forced into the liquid passageway by capillary force. The at least one heater may be arranged such that during vaping, only the small amount of liquid aerosol-forming substrate within the liquid passageway, and not the liquid within the housing, is heated. The heating elements may comprise a coil substantially surrounding at least a portion of a liquid passageway.

The heating element may comprise an inductive heating element. Inductive heating elements are described in more detail below, in relation to the cartridge.

The aerosol-generator may comprise one or more vibratable elements and one or more actuators arranged to excite vibrations in the one or more vibratable elements. The one or more vibratable elements may comprise a plurality of passages through which aerosol-forming substrate may pass and become atomized. The one or more actuators may comprise one or more piezoelectric transducers.

The aerosol-generator may comprise one or more capillary wicks for conveying liquid aerosol-forming substrate held in the liquid storage portion to the one or more elements of the aerosol-generator. The liquid aerosol-forming substrate may have physical properties, including viscosity, which allow the liquid to be transported through the one or more capillary wicks by capillary action. The one or more capillary wicks may have any of the properties of structures described above relating to the capillary material.

The one or more capillary wicks may be arranged to contact liquid held in the liquid storage portion. The one or more capillary wicks may extend into the liquid storage portion. In this case, during vaping, liquid may be transferred from the liquid storage portion to the one or more elements of the aerosol-generator by capillary action in the one or more capillary wicks. The one or more capillary wicks may have a first end and a second end. The first end may extend into the liquid storage portion to draw liquid aerosol-forming substrate held in the liquid storage portion into the aerosol generator. The second end may extend into an air passage of the aerosol-generating system. The second end may comprise one or more aerosol-generating elements. The first end and the second end may extend into the liquid storage portion. One or more aerosol-generating elements may be arranged at a central portion of the wick between the first and second ends. During vaping, when the one or more aerosol-generating elements are activated, the liquid aerosol-forming substrate in the one or more capillary wicks is atomized and/or vaporized at and around the one or more aerosol-generating elements.

The aerosol-generator may comprise one or more heating wires or filaments encircling a portion of one or more capillary wicks. The heating wire or filament may support the encircled portion of the one or more capillary wicks.

During vaping, atomized aerosol-forming substrate may be mixed with and carried in air flow through an air passage of the aerosol-generating system. The capillary properties of the one or more capillary wicks, combined with the properties of the liquid substrate, may ensure that, during vaping when there is sufficient aerosol-forming substrate, the wick is always wet with liquid aerosol-forming substrate in the area of the aerosol-generator.

The aerosol-generating system may comprise one or more power supplies. The power supply may be a battery. The battery may be a Lithium based battery, for example a Lithium-Cobalt, a Lithium-Iron-Phosphate, a Lithium Titanate or a Lithium-Polymer battery. The battery may be a Nickel-metal hydride battery or a Nickel cadmium battery. The power supply may be another form of charge storage device such as a capacitor. The power supply may require recharging and be configured for many cycles of charge and discharge. The power supply may have a capacity that allows for the storage of enough energy for one or more vaping experiences; for example, the power supply may have sufficient capacity to allow for the continuous generation of aerosol for a period of around six minutes, corresponding to the typical time taken to smoke a conventional cigarette, or for a period that is a multiple of six minutes. In another example embodiment, the power supply may have sufficient capacity to allow for a desired (or, alternatively a predetermined) number of puffs or discrete activations of the heating element and actuator.

The aerosol-generating system may comprise a control system configured to operate the aerosol-generator. The control system configured to operate the aerosol-generator may be the control system configured to identify the liquid aerosol-forming substrate held in the liquid storage portion. The control system configured to operate the aerosol-generator may be distinct of the control system configured to identify the liquid aerosol-forming substrate held in the liquid storage portion. The control system configured to operate the aerosol-generator may comprise similar components to the control system configured to identify the liquid held in the liquid storage portion.

The aerosol-generating system may comprise a temperature sensor in communication with the control system. The temperature sensor may be adjacent to the liquid storage portion. The temperature sensor may be a thermocouple. At least one element of the aerosol-generator may be used by the control system to provide information relating to the temperature. The temperature dependent resistive properties of the at least one element may be known and used to determine the temperature of the at least one element in a manner known to the skilled person. The control system may be configured to account or compensate for the effect of temperature on the electrical load between the first electrode and the second electrode using measurements of temperature from the temperature sensor.

The aerosol-generating system may comprise a puff detector in communication with the control electronics. The puff detector may be configured to detect when an adult vaper draws on the mouthpiece. The control electronics may be configured to control power to the aerosol-generator in dependence on the input from the puff detector.

The control system may comprise a tilt sensor. The tilt sensor may be configured to sense the orientation of the liquid storage portion. The aerosol-generating system may comprise a control system configured to receive sensed orientation information from the tilt sensor and to determine the orientation of the liquid storage portion. By determining the orientation of the liquid storage portion, the control system may be configured to determine whether the liquid aerosol-forming substrate held in the liquid storage portion is substantially perpendicular to the first electrode and the second electrode. The control system may be configured to identify the liquid aerosol-forming substrate held in the liquid storage portion when the liquid aerosol-forming substrate held in the liquid storage portion is substantially perpendicular to the first and second electrodes, such as when the liquid storage portion is determined to be upright.

The liquid aerosol-forming substrate may be subject to gravitational and acceleration forces that move the liquid aerosol-forming substrate to different sections of the liquid storage portion. Provided that the entire liquid storage portion is between the first and second electrodes, the measurement of the electrical quantity should not be affected.

The aerosol-generating system may comprise an input, such as a switch or button. This enables the adult vaper to turn the system on. The switch or button may activate the aerosol-generator. The switch or button may initiate aerosol generation. The switch or button may prepare the control electronics to await input from the puff detector.

The aerosol-generating system may comprise at least one indicator, for indicating the determined liquid aerosol-forming substrate identity to an adult vaper. The indicator may comprise one or more of lights, such as light emitting diodes (LEDs), a display, such as an LCD display, and a loudspeaker or buzzer. The control system may be configured to indicate the determined liquid aerosol-forming substrate identity to an adult vaper with the indicator. The control system may be configured to light one or more of the lights depending on the determined strength of liquid aerosol-forming substrate, display a type or strength of liquid aerosol-forming substrate on the display or emit sounds via the loudspeaker or buzzer to indicate determination of an authorized or unauthorized liquid aerosol-forming substrate.

The aerosol-generating system may comprise a housing. The housing may be elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. The material may be light and non-brittle.

The housing may comprise a cavity for receiving the power supply. The housing may comprise a mouthpiece. The mouthpiece may comprise at least one air inlet and at least one air outlet. The mouthpiece may comprise more than one air inlet. One or more of the air inlets may reduce the temperature of the aerosol before it is delivered to an adult vaper and may reduce the concentration of the aerosol before it is delivered to an adult vaper.

The aerosol-generating system may be portable. The aerosol-generating system may have a size comparable to a cigar or a cigarette. The aerosol-generating system may have a total length ranging from about 30 mm to about 150 mm. The aerosol-generating system may have an external diameter ranging from about 5 mm to about 30 mm.

The aerosol generating system may be an electrically operated vaping system. The aerosol-generating system may be an electronic cigarette or an electronic cigar.

The aerosol-generating system may comprise a main unit and a cartridge. The cartridge comprises the liquid storage portion for holding the liquid aerosol-forming substrate. The main unit may be configured to removably receive the cartridge. The first electrode and the second electrode may be arranged such that a portion of the liquid storage portion of the cartridge is between the first electrode and the second electrode when the cartridge is received by the main unit.

The main unit may comprise one or more power supplies. The main unit may comprise the aerosol-generator.

The cartridge may comprise the aerosol-generator. Where the cartridge comprises the aerosol-generator, the cartridge may be referred to as a tartomizer.

The aerosol-generating system may comprise an aerosol-generating component comprising the aerosol-generator. The aerosol-generating component may be separate of the main unit and the cartridge. The aerosol-generating component may be removably receivable by at least one of the main unit and the cartridge.

The main unit may comprise the first electrode and the second electrode. The cartridge may comprise the first electrode and the second electrode. The main unit may comprise one of the first electrode and the second electrode. The cartridge may comprise one of the first electrode and the second electrode. Arranging one of the first electrode and the second electrode on the main unit and arranging the other of the first electrode and the second electrode on the cartridge may enable identification of the cartridge. In other words, the presence or absence of an electrode on the cartridge may be used to verify whether the cartridge received by the main unit is a genuine or authentic cartridge from the manufacturer of the main unit. The type of electrode or measurements between the electrode of the main unit and the electrode of the cartridge may also be used to identify the type of cartridge received by the main unit or the type of liquid aerosol-forming substrate held in the liquid storage portion of the cartridge. The control system may be configured to determine the presence or absence of an electrode in the cartridge. The control system may be configured to determine the identity the cartridge based on the presence or absence of an electrode in the cartridge. The control system may also be configured to determine whether the cartridge has been correctly received by the main unit based on the presence or absence of an electrode in the cartridge.

The control system may be configured to identify the cartridge based on measured electrical quantity information between the first electrode and the second electrode. In other words, the control system may be configured to recognise an authentic cartridge. This may enable the aerosol-generating system or adult vaper to control operation of the aerosol-generating system to optimize atomization and/or vaporization of the liquid aerosol-forming substrate. This may enable a main unit to reduce and/or substantially prevent counterfeit cartridges from being used with the main unit.

Identification of a cartridge or a liquid aerosol-forming substrate held in a liquid storage portion of a cartridge may be straightforward for brand new cartridges, where the amount of liquid aerosol-forming substrate held in the liquid storage portion may be known. The control system may be configured to determine when a new cartridge is received by the main unit. The main unit may comprise a switch configured to activate on receipt of a cartridge by the main unit, or to be activated by an adult vaper on receipt of a new cartridge by the main unit.

The aerosol-generator may comprise heating elements substantially as described above. The heating elements may be inductive heating elements, such that no electrical contacts are formed between the cartridge and the main unit. The main unit may comprise an inductor coil and a power supply configured to provide high frequency oscillating current to the inductor coil. The cartridge may comprise a susceptor element positioned to heat the aerosol-forming substrate. As used herein, a high frequency oscillating current means an oscillating current having a frequency of between 10 kHz and 20 MHz.

The cartridge may be removably coupled to the main unit. The cartridge may be removed from the main unit when the aerosol-forming substrate has been consumed. The cartridge may be disposable. The cartridge may be reusable. The cartridge may be refillable with liquid aerosol-forming substrate. The cartridge may be replaceable in the main unit. The main unit may be reusable.

The cartridge may be manufactured at low cost, in a reliable and repeatable fashion. As used herein, the term 'removably coupled' is used to mean that the cartridge and the main unit can be coupled and uncoupled from one another without significantly damaging either the main unit or cartridge.

The cartridge may have a simple design. The cartridge may have a housing within which a liquid aerosol-forming substrate is held. The cartridge housing may be a rigid housing. The housing may comprise a material that is impermeable to liquid.

The cartridge may comprise a lid. The lid may be peelable before coupling the cartridge to the main unit. The lid may be piercable.

The main unit may comprise a cavity for receiving the cartridge. The main unit may comprise a cavity for receiving the power supply.

The main unit may comprise the aerosol-generator. The main unit may comprise one or more control systems of the aerosol-generating system. The main unit may comprise the power supply. The power supply may be removably coupled to the main unit.

The main unit may comprise the mouthpiece. The mouthpiece may comprise at least one air inlet and at least one air outlet. The mouthpiece may comprise more than one air inlet.

The main unit may comprise a piercing element for piercing the lid of the cartridge. The mouthpiece may comprise the piercing element. The mouthpiece may comprise at least one first conduit extending between the at least one air inlet and a distal end of the piercing element. The mouthpiece may comprise at least one second conduit extending between a distal end of the piercing element and the at least one air outlet. The mouthpiece may be arranged such that during vaping, when an adult vaper draws on the mouthpiece, air flows along an air passage extending from the at least one air inlet, through the at least one first conduit, through a portion of the cartridge, through the at least one second conduit and exits the at least one outlet. This may improve airflow through the main unit and enable the aerosol to be delivered to the adult vaper more easily.

During vaping, an adult vaper may insert a cartridge as described herein into the cavity of a main unit as described herein. The adult vaper may attach the mouthpiece to the main body of the main unit, which may pierce the cartridge with the piercing portion. The adult vaper may activate the main unit by pressing the switch or the button. The adult vaper may draw on the mouthpiece to draw air into the main unit through the one or more air inlets. The air may pass over a portion of the aerosol-generator, entraining atomized and/or vaporized aerosol-forming substrate, and exit the main unit through the air outlet in the mouthpiece to be inhaled by the adult vaper.

A kit of parts may be provided, comprising a cartridge, a main unit, substantially as described above. An aerosol-generating system according to at least one example embodiment may be provided by assembling the cartridge, the aerosol-generator and the main unit. The components of the kit of parts may be removably connected. The components of the kit of parts may be interchangeable. Components of the kit of parts may be disposable. Components of the kit of parts may be reusable.

There may be provided a main unit for an aerosol-generating system according to at least one example embodiment. The main unit may comprise the control system and at least one of the first electrode and the second electrode.

There may be provided a cartridge for an aerosol-generating system according to at least one example embodiment. The cartridge may comprise: the liquid storage portion; and at least one of the first electrode and the second electrode. The cartridge may comprise a housing for holding a liquid aerosol-forming substrate in the liquid storage portion. The cartridge may comprise aerosol-generator configured to receive liquid aerosol-forming substrate from the liquid storage portion.

According to at least one example embodiment, a method of identifying liquid aerosol-forming substrate held in a liquid-storage portion of an aerosol-generating system comprises: holding a liquid aerosol-forming substrate in a liquid storage portion of an aerosol-generating system; arranging at least a portion of the liquid storage portion between a first electrode and a second electrode, the portion of the liquid storage portion between the first electrode and the second electrode holding liquid aerosol-forming substrate when liquid aerosol-forming substrate is held in the liquid storage portion; measuring an electrical quantity between the first electrode and the second electrode; and identifying the liquid aerosol-forming substrate held in the liquid storage portion based on the measured electrical quantity information.

Features such as the liquid storage portion and the first electrode and the second electrode may be the same as those described in relation to the example embodiments described above.

The identifying the liquid aerosol-forming substrate held in the liquid storage portion may comprise comparing the measured electrical quantity information to reference electrical quantity information. The reference electrical quantity information may be electrical quantity information previously measured by the control system. The reference electrical quantity information may be stored in a memory of the aerosol-generating system. The reference electrical quantity information may be stored in a lookup table.

The reference electrical quantity information may be measured by the control system in a calibration procedure. The calibration procedure may be performed to populate the lookup table. In the calibration procedure, the liquid storage portion may be loaded with desired (or, alternatively a predetermined) liquid aerosol-forming substrates. The electrical quantity between the first electrode and the second electrode may be measured when the liquid storage portion is loaded with the known liquid aerosol-forming substrates. The measured electrical quantity information may be stored in a lookup table and associated in the lookup table with the known identity of the liquid aerosol-forming substrate held in the liquid storage portion at the time of the measurement.

The calibration procedure may be performed in the factory before the aerosol-generating system is distributed. The calibration procedure may be performed by an adult vaper before the first vaping of the aerosol-generating system.

A method of controlling operation of aerosol-generator of an aerosol-generating system may comprise: holding a liquid aerosol-forming substrate in a liquid storage portion of an aerosol-generating system; arranging at least a portion of the liquid storage portion between a first electrode and a second electrode, the portion of the liquid storage portion between the first electrode and the second electrode holding liquid aerosol-forming substrate when liquid aerosol-forming substrate is held in the liquid storage portion; measuring an electrical quantity between the first electrode and the second electrode; identifying the liquid aerosol-forming substrate held in the liquid storage portion based on the measured electrical quantity information; and controlling operation of aerosol-generator of the aerosol-generating system based on the determined identity of the liquid aerosol-forming substrate held in the liquid storage portion.

Features described in relation to one example embodiment may also be applicable to other example embodiments. Features described in relation to the method may be applicable to the aerosol-generating system and features corresponding to the aerosol-generating system may be applicable to the method.

FIG. 1 is a schematic illustration of an aerosol-generating system. FIG. 1 is schematic in nature, and the components shown are not necessarily to scale either individually or relative to one another. The aerosol-generating system comprises a main unit 100, which is preferably reusable, in cooperation with a cartridge 200, which is preferably disposable. The aerosol-generating system shown in FIG. 1 is an electrically operated vaping system.

The main unit 100 comprises a main housing 101. The housing is substantially cylindrical and has a longitudinal length of about 100 mm and an external diameter of about 20 mm, comparable to a cigar. The main unit 100 comprises an electric power supply in the form of a lithium ion phosphate battery 102 and a control system in the form of control electronics 104. The main housing 101 also defines a cavity 112 into which the cartridge 200 is received.

The main unit 100 also includes a mouthpiece portion 120 including an outlet 124. The mouthpiece portion is connected to the main housing 101 by a hinged connection in this example but any kind of connection may be used, such as a snap fitting or a screw fitting. One or more air inlets 122 are provided between the mouthpiece portion 120 and the main body 101 when the mouthpiece portion is in a closed position, as shown in FIG. 1.

Within the mouthpiece portion is a flat spiral inductor coil 110. The coil 110 is formed by stamping or cutting a spiral coil from a sheet of copper. The coil 110 is positioned between the air inlets 122 and the air outlet 124 so that air drawn through the inlets 122 to the outlet 124 passes through the coil.

The cartridge 200 (shown in schematic form in FIG. 1) comprises a rigid housing 204 defining a liquid storage portion 201. The liquid storage portion 201 contains a liquid aerosol-forming substrate (not shown). The housing 204 of the cartridge 200 is fluid impermeable but has an open end covered by a permeable susceptor element 210. The permeable susceptor element 210 comprises a ferrite mesh, comprising a ferrite steel. The aerosol-forming substrate can form a meniscus in the interstices of the mesh. When the cartridge 200 is engaged with the main unit and is received in the cavity 112, the susceptor element 210 is positioned adjacent the flat spiral coil 110. The cartridge 200 may include keying features to ensure that it cannot be inserted into the main unit upside-down.

During vaping, an adult vaper puffs on the mouthpiece portion 120 to draw air though the air inlets 122 into the mouthpiece portion 120 and out of the outlet 124. The main unit includes a puff sensor 106 in the form of a microphone, as part of the control electronics 104. A small air flow is drawn through sensor inlet 121 past the microphone 106 and up into the mouthpiece portion 120 when an adult vaper puffs on the mouthpiece portion. When a puff is detected, the control electronics provide a high frequency oscillating current to the coil 110. This generates an oscillating magnetic field as shown in dotted lines in FIG. 1. An LED 108 is also activated to indicate that the main unit is activated. The oscillating magnetic field passes through the susceptor element, inducing eddy currents in the susceptor element. The susceptor element heats up as a result of Joule heating and as a result of hysteresis losses, reaching a temperature sufficient to vaporize the aerosol-forming substrate close to the susceptor element. The vaporized aerosol-forming substrate is entrained in the air flowing from the air inlets to the air outlet and cools to form an aerosol within the mouthpiece portion. The control electronics supplies the oscillating current to the coil for a desired (or, alternatively a predetermined) duration, in this example five seconds, after detection of a puff and then switches the current off until a new puff is detected.

The cartridge 200 has generally cylindrical shape and the susceptor element spans a circular open end of the cartridge housing. It will be appreciated that other configurations are possible. In at least one example embodiment, the susceptor element may be a strip of steel mesh 220 that spans a rectangular opening in the cartridge housing 204.

In at least one example embodiment, as shown in FIG. 1, the aerosol-generating system may rely on inductive heating. Further examples of suitable inductive heating elements and explanation of the operation of inductive heating systems are described in WO 2015/177046 A1, the entire content of which is incorporated herein by reference thereto.

It will be appreciated that the aerosol-generating system may comprise other types of aerosol-generator. In at least one example embodiment, the aerosol-generator may comprise other aerosol-generator configured to atomise the liquid aerosol-forming substrate by heat. The aerosol-generator may comprise one or more resistive heating elements. The aerosol-generator may also comprise aerosol-generator configured to atomise the liquid aerosol-forming substrate by vibration. The aerosol-generator may comprise one or more vibratable elements and actuators.

Several examples of cartridges suitable for main units of aerosol-generating systems, such as the main unit shown in FIG. 1, are shown in FIGS. 2 to 12. The cartridges shown in FIGS. 2 to 12 comprise liquid storage portions and electrode arrangements according to the present invention.

Figures 2, 3, 4, 5:
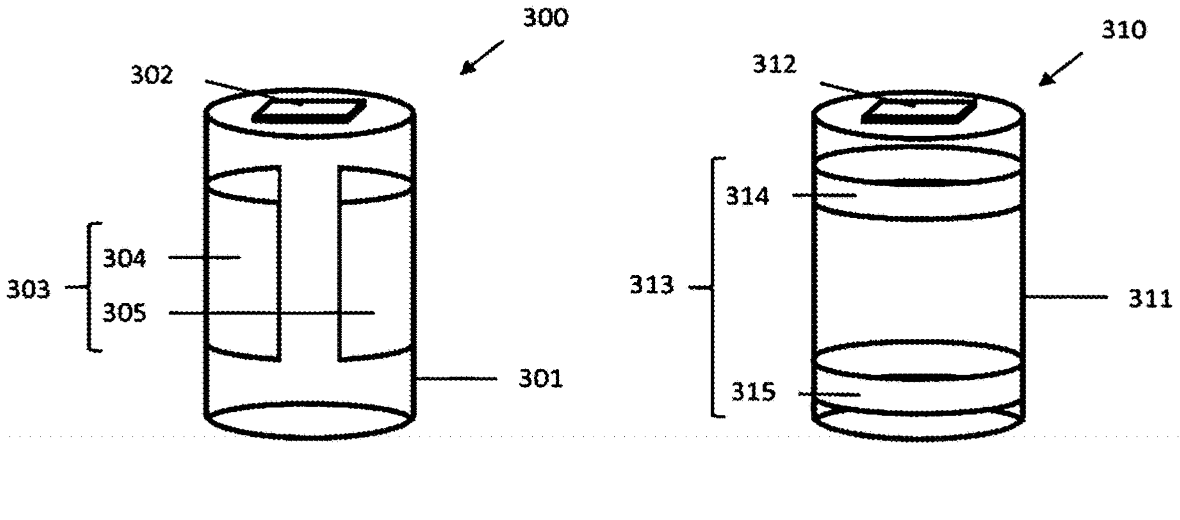
FIG. 2 is an illustration of a liquid storage portion for an aerosol-generating system according to at least one example embodiment.
FIG. 3 is an illustration of a liquid storage portion for an aerosol-generating system according to at least one example embodiment.
FIG. 4 is an illustration of a liquid storage portion for an aerosol-generating system according to at least one example embodiment.
FIG. 5 is an illustration of a liquid storage portion for an aerosol-generating system according to at least one example embodiment.

The cartridge 300 shown in FIG. 2 comprises a substantially cylindrical housing 301, having a closed end and a substantially open end. The housing is rigid and substantially fluid impermeable, and defines a liquid storage portion that is configured to hold liquid aerosol-forming substrate (not shown) either freely or held in a carrier material.

Aerosol-generating elements 302 are provided over the open end of the housing 301. In at least one example embodiment, the aerosol-generating elements comprise a ferrite mesh susceptor. A sensor 303 is on an inner surface of the housing 301, within the liquid storage portion. The sensor comprises a first electrode 304 and a second electrode 305. The first and second electrodes 304, 305 are substantially identical and comprise arcuate metal plates at opposite sides of housing 301. Each electrode 304, 305 substantially circumscribes about half the circumference of the inner surface of the housing 301 and extends substantially the length of the housing 301, from the open end to the closed end. The electrodes 304, 305 are on the housing with a gap between the sides of the plates, to ensure that the plates 304, 305 are not in an electrically conductive relationship. This arrangement enables the sensor 303 to sense electrical quantities of the entire liquid storage portion.

Electrical contacts (not shown) extend through the housing, from the outer surface to the inner surface of each of the plates. When the cartridge 300 is received in a cavity of a main unit, the contacts of the cartridge 300 abut complimentary contacts in the cavity of the main unit to electrically connect the sensor 303 to a power supply and a control system of the main unit.

The cartridge 310 shown in FIG. 3 has a substantially similar construction to the cartridge 300 shown in FIG. 2. The cartridge 310 comprises a substantially cylindrical housing 311 defining a liquid storage portion, and an aerosol-generating element 312 over an open end. The cartridge 300 comprises a sensor 313 around at an outer surface of the liquid storage portion. The sensor 313 comprises a first electrode 314 and a second electrode 315. The first and second electrodes 314, 315 are substantially identical and comprise copper rings circumscribing the outer surface of the housing 311. The first electrode 314, 315 is arranged towards the open end of the housing 311 and the second electrode 315 is arranged towards the closed end so that the sensor 313 is configured to sense electrical quantities of the entire liquid storage portion.

The cartridge 320 shown in FIG. 4 has a substantially similar construction to the cartridge 310 shown in FIG. 3. The cartridge 320 comprises a substantially cylindrical housing 321, having an open end and a closed end, and an aerosol-generating element 322 arranged over the open end. The cartridge 320 comprises a sensor 323 comprising a first electrode 324 comprising a ring electrode at an inner surface of the housing 321, and a second electrode comprising the aerosol-generating element 322.

The cartridge 330 shown in FIG. 5 has a substantially similar construction to the cartridges 300, 310 and 320 shown in FIGS. 2, 3 and 4. The cartridge 330 comprises a substantially cylindrical housing 331, having an open end and a closed end, and an aerosol-generating element 332 over the open end. The cartridge 330 comprises a sensor 333 at an inner surface of the housing 321. The sensor 333 comprises a first electrode 334 and a second electrode 335. The first and second electrodes 334, 335 are point electrodes extending through opposing sides of the housing 331 at the same position along the length of the housing 331. This minimizes and/or reduces the distance between the electrodes and may improve the sensitivity of the sensor 333. Where carrier material is provided in the liquid storage portion, the point electrodes 334, 335 may be in contact with the carrier material. Liquid aerosol-forming substrate held in the liquid storage portion permeates through the carrier material. A change in the amount of liquid aerosol-forming substrate held in the liquid storage portion affects the saturation of the carrier material, and changes the electrical quantities of the carrier material. This enables the point electrodes 334, 335 to sense electrical quantities of the entire liquid storage portion.

Figures 6, 7, 8:
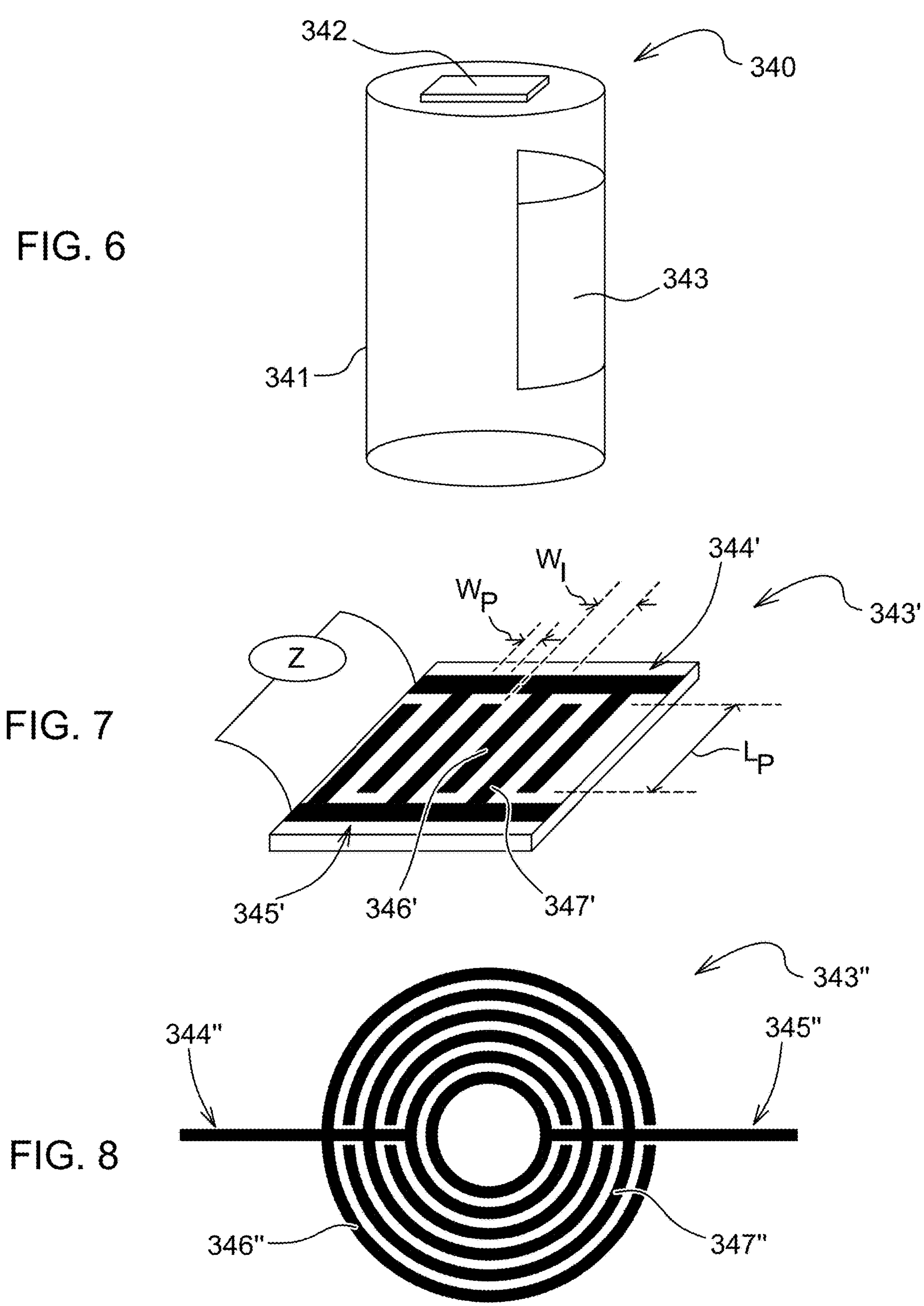
FIG. 6 is an illustration of a liquid storage portion for an aerosol-generating system according to at least one example embodiment.
FIG. 7 is an illustration of a sensor comprising interdigitated electrodes according to at least one example embodiment.
FIG. 8 is an illustration of a sensor comprising interdigitated electrodes according to at least one example embodiment.

The cartridge 340 shown in FIG. 6 has a substantially similar construction to the cartridges 300, 310, 320 and 330 shown in FIGS. 2, 3, 4 and 5. The cartridge 340 comprises a substantially cylindrical housing 341, having an open end and a closed end, and an aerosol-generating element 342 over the open end. The cartridge 340 comprises a sensor 343 at an inner surface of the housing 341. The sensor 343 comprises first and second electrodes (not shown) on a platform. The platform comprises an electrically insulating polymer sheet, having a similar size and shape to one of the electrodes 304, 305 of the cartridge 300 shown in FIG. 2. The platform is adhered to the inner surface of the housing 343 and is sufficiently flexible to conform to the shape of the housing 343.

In at least one example embodiment, the first and second electrodes may be on a platform, such as the platform of the sensor 343 as shown in FIG. 7. The sensor 343' comprises a first electrode 344' and a second electrode 345' that are interdigitated. Each electrode 344', 345' is substantially identical and comprises a linear main track and a plurality of linear protrusions extending away from the main track, in a direction substantially perpendicular to the main track. Each electrode 344', 345' comprises 125 protrusions, each protrusion having a length $L_P$, of about 6760 μm, and a width $W_P$, of about 10 μm. Neighbouring protrusions are spaced apart by interspaces having a width $W_I$, of about 30 μm.

The main track of the first electrode 344' and the main track of the second electrode 345' are arranged in parallel on the platform, at a separation of about 6780 μm. The first electrode 344' is arranged with its protrusions 346' facing the second electrode 345' and within the interspaces of the second electrode 345'. The second electrode 345' is arranged with its protrusions 347' facing the first electrode 344' and within the interspaces of the first electrode 344'. In at least one example embodiment, a consistent spacing of about 10 μm is provided between the first electrode 344' and the second electrode 345' along the entire length of the electrodes 344', 345'.

In at least one example embodiment, the first and second electrodes are arranged on a platform, such as the platform of the sensor 343, is shown in FIG. 8. The sensor 343" comprises a first electrode 344" and a second electrode 345" that are interdigitated. Each electrode 344", 345" comprises a linear main track and a plurality of pairs of arcuate protrusions, extending in opposite directions away from the main track. Each electrode 344", 345" comprises about 50 pairs of arcuate protrusions. Each protrusion has a width of about 10 μm. Each pair of protrusions forms an incomplete circle that is not joined at the distalmost end from the main track. Neighbouring pairs of protrusions are spaced apart by interspaces having a width of about 30 μm. The distalmost protrusion of the second electrode 345" comprises a complete circle.

The main track of the first electrode 344" and the main track of the second electrode 345" are arranged in coaxial alignment on the platform parallel on the platform, with the protrusions 346" of the first electrode 344" within the interspaces of the second electrode 345" and the protrusions 347" of the second electrode 345" within the interspaces of the first electrode 344". The distalmost protrusion of the first electrode 344" substantially surrounds the distalmost protrusion of the second electrode 345". In this arrangement, a consistent spacing of about 10 μm is provided between the first electrode 344' and the second electrode 345' along the entire length of the electrodes 344', 345'.

Figures 9, 10, 11:
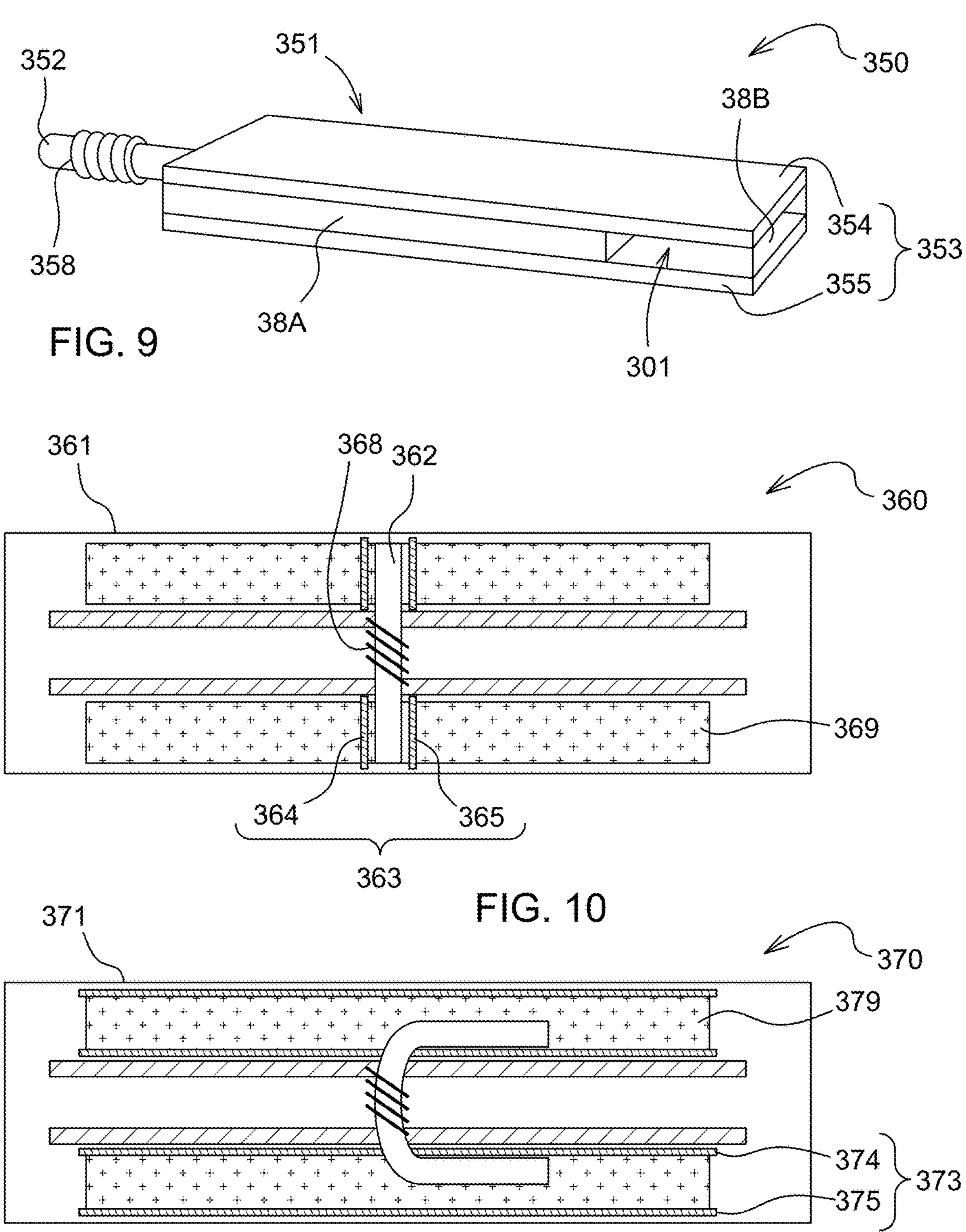
FIG. 9 is an illustration of a liquid storage portion for an aerosol-generating system according to at least one example embodiment.
FIG. 10 is an illustration of a liquid storage portion for an aerosol-generating system according to at least one example embodiment.
FIG. 11 is an illustration of a liquid storage portion for an aerosol-generating system according to at least one example embodiment.

The cartridge 350 shown in FIG. 9 comprises a rigid housing 351 defining a liquid storage portion. The housing 351 comprises substantially planar sides. The internal volume of the housing 301 is sufficiently narrow that capillary forces act on a liquid aerosol-forming substrate held in the liquid storage portion. A sensor 353 comprises a first plate electrode 354 and a second plate electrode 355 at opposite sides of the liquid storage portion. The electrodes 354, 355 form substantially parallel electrode plates having a length ranging from about 25 mm to about 30 mm and a width ranging from about 5 mm to about 7 mm. This corresponds to a cross-sectional area ranging from about 25 mm×5 mm to about 30 mm×7 mm. The separation between the first and second electrodes 344, 345 ranges from about 2 mm to about 3 mm.

The cartridge 350 further comprises aerosol-generator in the form of a wick 352 extending from an end of the liquid storage portion and a heating coil 358 wound around the wick 352 at the distal end. During vaping, the coil 358 heats the wick 352 and atomises liquid aerosol-forming substrate in the wick 352. This draws liquid aerosol-forming substrate held in the liquid storage portion to the wick end of the liquid storage portion. The capillary forces caused by the narrow separation between the first and second electrodes 354, 355 do not enable the liquid aerosol-forming substrate held in the liquid storage portion to move freely. As a result, liquid aerosol-forming substrate collects at the wick end of the liquid storage portion and the liquid storage portion may be notionally divided into two sections, a first section 38A towards the wick end that is filled with liquid aerosol-forming substrate and a second section 38B opposite the wick end that is filled with air. As the liquid aerosol-forming substrate is consumed during vaping, the second section 38B filled with air increases in size and the first section 38A filled with liquid aerosol-forming substrate decreases in size.

The cartridge 360 shown in FIG. 10 comprises a substantially cylindrical housing 361 comprising a central airflow passage extending there through. A liquid storage portion is defined between the housing 361 and the central airflow passage, and comprises an annular body of carrier material. The cartridge 360 comprises aerosol-generator in the form of a wick 362 extending across the airflow passage and a heating coil 368 in the air passage and wound around the wick 362. The cartridge 360 comprises a sensor 363 comprising a first electrode 364 and a second electrode 365 at opposite sides of the wick. During vaping, the coil 368 heats the wick 362 and atomizes liquid aerosol-forming substrate in the wick 362. This draws liquid aerosol-forming substrate held in the carrier material to the wick and changes the saturation of both the wick 362 and the carrier material. As the saturation of the wick changes, the electrical load between the electrodes, 364, 365 changes.

The cartridge 370 shown in FIG. 11 has a similar construction and arrangement to the cartridge 360 shown in FIG. 10. The cartridge 370 comprises a sensor 373 comprising a first, circularly cylindrical plate electrode 374 around the inner surface of the annular body of carrier material and a second, circularly cylindrical plate electrode 375 around the outer surface of the body of carrier material. The first and second electrodes 375, 374 form concentric circularly cylindrical plates bounding the inner and outer surfaces of the annular body of carrier material. During vaping, the coil heats the wick and atomizes liquid aerosol-forming substrate in the wick, which draws liquid aerosol-forming substrate held in the carrier material to the wick. This changes the saturation of the carrier material, which changes the electrical load between the electrodes 374, 375.

Figure 12:
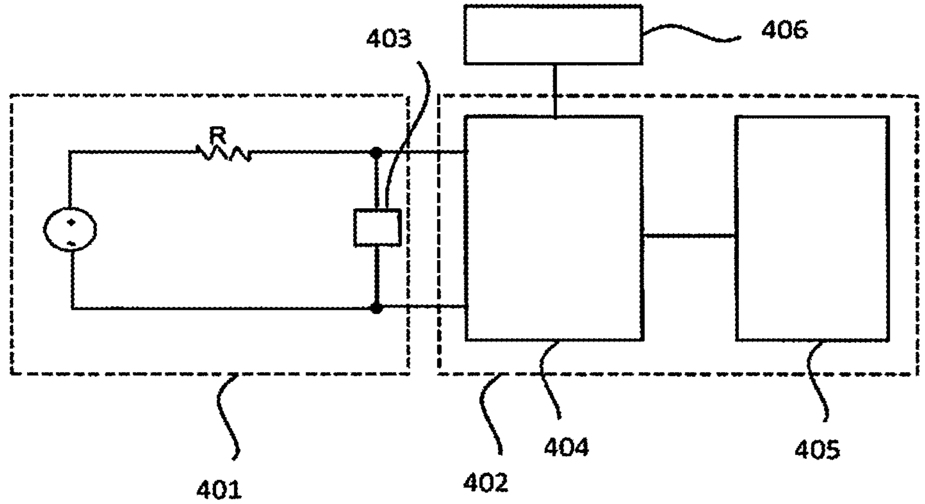
FIG. 12 is a schematic circuit diagram for a sensor according to at least one example embodiment.

FIG. 12 shows a schematic circuit diagram of a sensor circuit 401 and control system circuit 402 for an aerosol-generating system according to the present invention. The sensor circuit 401 comprises a sensor 403, in series with a resistor R and a dedicated sensor power supply to supply an alternating voltage to the sensor 403 at a desired (or, alternatively a predetermined) frequency. The control system circuit 402 comprises control electronics comprising a controller 404 and memory 405. The control electronics are connected to a power supply 406.

In other example embodiments (not shown) the sensor 403 may be connected to the power supply 406, which may be configured to supply power to the sensor circuit 401 and the control system circuit 402. The power supply 406 may also be configured to supply power to the aerosol-generator of the aerosol-generating system and the control system circuit 402 may be configured to control operation of the aerosol-generator.

In at least one example embodiment, an aerosol-generating system comprises one of the cartridges shown in FIGS. 2 to 12. During vaping, the aerosol-generating system is turned on by the adult vaper activating a switch, and a control system of the aerosol-generating system supplies an oscillating measurement signal to the first and second electrodes. The control system receives impedance information from the first and second electrodes and compares the measured impedance information to reference impedance information stored in a lookup table in a memory of the control system. The control system matches the measured impedance information to a stored reference impedance information in the lookup table. The stored reference impedance information is associated with a known composition of liquid aerosol-forming substrate. The control system indicates to an adult vaper that the composition of liquid aerosol-forming substrate is known by displaying the identity of the liquid aerosol-forming substrate on an LED display of the aerosol-generating system. In some example embodiments, the control system is configured to control the power supply to aerosol-generator of the aerosol-generating system based on the determined identity of the liquid aerosol-forming substrate.

If the control system is unable to match the sensed impedance information to a stored reference impedance information, the control system displays to an adult vaper that the liquid aerosol-forming substrate is unknown or unauthorized. In some example embodiments, the control system is configured to reduce and/or substantially prevent operation of aerosol-generator of the aerosol-generating system if the identity of the liquid aerosol-forming substrate is unknown.

A calibration procedure may be performed for each aerosol-generating system. In a calibration procedure, liquid aerosol-forming substrates having known compositions may be introduced into the liquid storage portion, and at least one of the inductance, resistance or capacitance may be measured. The measurements may be stored in a lookup table in a memory of the control system, and each measurement associated with an identity of liquid aerosol-forming substrate.

It will be appreciated that in other example embodiments (not shown), the control system may be configured to supply a measurement signal to the first electrode and the second electrode that is not oscillating. In other words, a direct voltage may be supplied to the first and second electrodes. In these example embodiments, the control system may be configured to measure the resistance between the first and second electrodes.

It will be appreciated that the relationship between the impedance, capacitance and resistance and the identity of the liquid aerosol-forming substrate will depend on the type and relative positions of the electrodes relative to each other and the liquid storage portion.

It will be appreciated that in other embodiments (not shown) that the cartridges described in relation to FIGS. 2 to 12 may not be cartridges, but rather may be integral parts of aerosol-generating systems, such as the aerosol-generating system shown in FIG. 1. It will also be appreciated that a main unit may be provided with sensors, such as the pairs of first and second electrodes shown in FIGS. 2 to 12, arranged to sense electrical quantities of liquid storage portions of cartridges received by the main units.

It will be appreciated that features described for one example embodiment may be provided in other example embodiments. In particular, it will be appreciated that cartridges and aerosol-generating systems according to the example embodiments may comprise more than one means of determining the identity of the liquid aerosol-forming substrate held in the liquid storage portion, such as more than one pair of first and second electrodes.

We claim:

1. An aerosol-generating system comprising:

a liquid storage portion configured to hold a liquid aerosol-forming substrate, the storage portion in contact with a wick;

a first electrode;

a second electrode spaced from the first electrode, at least a portion of the liquid storage portion being arranged between the first electrode and the second electrode, the portion of the liquid storage portion arranged between the first electrode and the second electrode contains the liquid aerosol-forming substrate when the liquid aerosol-forming substrate is held in the storage portion, the first electrode being arranged to circumscribe an entirety of a surface of the liquid storage portion at a first point, and the second electrode being arranged to circumscribe the entirety of the surface of the liquid storage portion at a second point, the first point and the second point are longitudinally spaced apart; and a control system configured to measure an electrical quantity of the liquid aerosol-forming substrate held within the liquid storage portion between the first electrode and the second electrode, and, in response to the measured electrical quantity of the liquid aerosol-forming substrate being within a range of reference of a plurality of range of references, identify the liquid aerosol-forming substrate held in the storage portion as corresponding to an approved producer.

2. The aerosol-generating system according to claim 1, wherein the control system is configured to identify the liquid aerosol-forming substrate held in the liquid storage portion by comparing the measured electrical quantity to reference electrical quantity information stored in the control system.

3. The aerosol-generating system according to claim 1, further comprising:

an aerosol-generator configured to receive the liquid aerosol-forming substrate from the liquid storage portion, and wherein the control system is further configured to control operation of the aerosol-generator based on the determined identity of the liquid aerosol-forming substrate held in the liquid storage portion.

4. The aerosol-generating system according to claim 1, wherein the first electrode and the second electrode are on a platform of electrically insulating material.

5. The aerosol-generating system according to claim 1, further comprising:

an aerosol-generator including one or more aerosol-generating elements, the one or more aerosol-generating elements including a heater, a vibratable element, an ultrasonic transducer, or any combination thereof, and wherein at least one of the aerosol-generating elements includes at least one of the first electrode and the second electrode.

6. The aerosol-generating system according to claim 1, further comprising:

a power supply configured to supply the first electrode and the second electrode with a measurement signal.

7. The aerosol-generating system according to claim 1, wherein the electrical quantity to be measured by the control system is impedance between the first electrode and the second electrode.

8. The aerosol-generating system according to claim 1, wherein the electrical quantity to be measured by the control system is resistance between the first electrode and the second electrode.

9. The aerosol-generating system according to claim 1, wherein the electrical quantity to be measured by the control system is capacitance between the first electrode and the second electrode.

10. The aerosol-generating system according to claim 1, wherein the system further comprises:

a cartridge including the liquid storage portion, and a main unit including the control system, the main unit configured to removably receive the cartridge, and the first electrode and the second electrode arranged such that a portion of the liquid storage portion of the cartridge is between the first electrode and the second electrode when the cartridge is received by the main unit.

11. The aerosol-generating system according to claim 10, wherein the cartridge comprises the first electrode and the second electrode.

12. The aerosol-generating system according to claim 10, wherein the main unit comprises the first electrode and the second electrode.

13. The aerosol-generating system according to claim 10, wherein the cartridge includes one of the first electrode and the second electrode, and the main unit comprises another one of the first electrode and the second electrode.

14. A method of identifying a liquid aerosol-forming substrate held in a liquid storage portion of an aerosol-generating system, the method comprising:

measuring an electrical quantity of the liquid aerosol-forming substrate held in the liquid storage portion between a first electrode and a second electrode, wherein a portion of a storage portion contains the aerosol-forming substrate between the first electrode and the second electrode, the first electrode being arranged to circumscribe an entirety of a surface of the liquid storage portion at a first point, the second electrode being arranged to circumscribe the entirety of the surface of the liquid storage portion at a second point, the first point and the second point are longitudinally spaced apart, and the liquid storage portion is in contact with a wick; and in response to the measured electrical quantity being within a range of reference of a plurality of range of references, identifying the liquid aerosol-forming substrate held in the liquid storage portion as corresponding to an approved producer.

15. The aerosol-generating system according to claim 1, wherein a carrier material is included in the liquid storage portion, and the first electrode and the second electrode are in direct contact with the carrier material.

16. The aerosol-generating system according to claim 1, wherein the first electrode and the second electrode are in direct contact with the liquid aerosol-generating substrate.

* * * * *